United States Patent [19]

Singh et al.

[11] Patent Number: 4,570,012

[45] Date of Patent: Feb. 11, 1986

[54] URETHANES FROM TERTIARY ARALKYL DIOLS

[75] Inventors: Balwant Singh; Peter S. Forgione, both of Stamford; Laurence W. Chang, Orange, all of Conn.

[73] Assignee: American Cyanamid Co., Stamford, Conn.

[21] Appl. No.: 582,145

[22] Filed: Feb. 24, 1984

Related U.S. Application Data

[63] Continuation of Ser. No. 457,083, Jan. 10, 1983, abandoned.

[51] Int. Cl.[4] .............. C07C 125/065; C07C 125/073
[52] U.S. Cl. .................................. 560/25; 560/27; 560/28; 560/29; 560/30; 260/453 P

[58] Field of Search ............. 560/25, 27, 28, 29, 560/30; 260/453 P

[56] References Cited

U.S. PATENT DOCUMENTS 3,404,170 10/1968 Ulrich ................... 560/25 X
4,439,616 3/1984 Singh et al. ............ 560/25

FOREIGN PATENT DOCUMENTS 283355 4/1965 Australia ................ 560/30

Primary Examiner—Bernard Helfin
Attorney, Agent, or Firm—William H. Calnan

[57] ABSTRACT

Production of tertiary aralkyl urethanes, such as tetramethyl xylylene diurethanes, by addition of corresponding diols and carbamic acid esters at moderate temperatures and in the presence of acid catalyst.

14 Claims, No Drawings

URETHANES FROM TERTIARY ARALKYL DIOLS

This application is a continuation, of application Ser. No. 457,083, filed Jan. 10, 1983 and now abandoned.

This invention relates to the manufacture of isocyanates and in particular provides a new route for the synthesis of tertiary aralkyl urethanes which are prepared from the corresponding tertiary hydroxy aralkyl compounds and from which the corresponding tertiary aralkyl isocyanates can be prepared.

A new synthesis of tertiary aralkyl isocyanates from the corresponding olefins is described in copending application Ser. No. 400,799, filed July 22, 1982, now U.S. Pat. No. 4,439,616. In accordance with that application the manufacture of a tertiary aralkyl isocyanate is by the preparation of the corresponding tertiary aralkyl carbamic acid ester of a lower aliphatic alcohol followed by the thermal cracking of such urethane to form the isocyanate and the free alcohol. It is an important object of this invention to provide an alternate route to the manufacture of tertiary aralkyl isocyanates through the same carbamic acid esters using tertiary hydroxy compounds as precursors. Thus in accordance with this invention, tertiary aralkyl diols are reacted with lower alkyl esters of carbamic acid to form the N-substituted tertiary aralkyl carbamic acid esters, which, as in the above noted copending application, can then be thermally cracked to give the corresponding isocyanates.

Since the esters of carbamic acid, such as methyl carbamate, the esters of N-substituted carbamic acids, such as the di-methyl ester of α,α,α,α,-tetramethylxylylene dicarbamic acid, and the polymers of poly isocyanates with polyols are all properly called urethanes, for the sake of clarity, herein an unsubstituted carbamic acid ester will be called "carbamate" or "carbamic acid ester"; a substituted carbamic acid ester will be called "urethane", "monourethane", "diurethane", "polyurethane" or "urethane ester"; and the polymers will be called "urethane polymers".

Urethanes which are useful in forming tertiary aralkyl isocyanates by thermal cracking in accordance with this invention are those described in the above noted copending application and are generally designated by the formula:

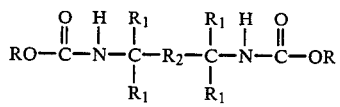

wherein R is an alkyl radical having from 1 to 18 or more carbon atoms; $R_1$ is an alkyl radical having from 1 to 3 carbon atoms; and $R_2$ represents an aromatic hydrocarbon moiety such as phenyl, biphenyl and naphthalyl and such an aromatic hydrocarbon moiety having substituents including halogen atoms, methyl and methoxy groups and substituents such as:

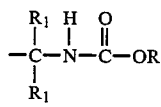

These urethanes are thus tertiary aralkyl urethanes in which R is a radical derived from an aliphatic alcohol, such as methanol, ethanol, isopropanol, 2-ethyl-hexanol-1 and n-octadecanol. Such alcohol is split off on thermal cracking of the urethane ester and can usually be recovered and recycled.

These tertiary aralkyl urethane esters in accordance with this invention are prepared by reaction of the carbamic acid ester of an alkyl or aralkyl alcohol and a tertiary aralkyl diol. The reaction of the diol and carbamate generally proceeds at moderate temperatures in the presence of an acid catalyst such as sulfuric acid, toluene sulfonic acid, dodecylbenzene sulfonic acid, hydrocarbon sulfate esters, hydrogen chloride, boron trifluoride, and other Lewis and Bronstead acids. The reaction takes place in the presence of solvents such as toluene, xylene, chlorobenzene and methylene dichloride, but also can take place in the absence of solvents. Generally, an excess of carbamate is preferred, but selective conversion of diol to mono-urethane can take place, if the amount of carbamate is limited, yielding a urethane ester having a mono-hydroxy or a mono-olefin functionality. Heat can be used to accelerate the reaction. Temperatures which are suitable range from about room temperature to about 150° C.

After formation of the urethane ester the reaction mixture is neutralized with base, such as CaO, $Na_2CO_3$, NaOH and the like, and thermally cracked to yield the isocyanate as described in the above noted copending application. The water formed by reaction of the diol and the carbamate or otherwise present in the system can be removed, following neutralization, by distillation prior to cracking. If excess of carbamate was employed this is preferably also distilled off at partial vacuum and recovered. Generally, water will be removed first in such distillation. The recovered carbamate can be recycled with water present, as water is formed in the system in any event. The reaction mixture of urethanes, unreacted carbamate ester, catalyst, water and by-products can also be separated by drowning in water, for example, in sodium carbamate solution to separate the urethane products as insolubles and also to neutralize the catalyst.

As in the above noted copending application, the urethane esters are then converted to the corresponding tertiary aralkyl isocyanates by thermal cracking. Yields are good, and alcohol recovery and removal are particularly high where the aliphatic alcohol group of the initial carbamic acid ester is methanol or other lower, preferably normal, alcohol.

Suitable diol precursors include para- and meta- α,α-,α',α'-tetramethyl-xylylene diols,(di-(1-hydroxy-1-methyl ethyl) naphthalenes, and other compounds having the general formula:

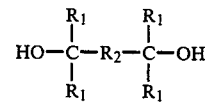

in which $R_1$ is an alkyl radical having from 1 to 3 carbon atoms, and $R_2$ represents an aromatic hydrocarbon moiety selected from phenyl, biphenyl and naphthalyl groups and such groups having halo, methyl and methoxy substituents and substituents of the formula:

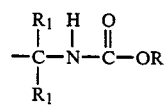

wherein $R_1$ has the same significance.

Generally, while the proportion of carbamic acid ester to diol can be stoichiometric, preferably the carbamate is in substantial excess and functions as solvent and catalyst moderator as well as reactant. It is preferred in accordance with this invention to use from 50% to 800% stoichiometric excess of carbamate, preferably about 300% excess carbamate.

The amount of catalyst required to promote the addition of tertiary aralkyl diol and carbamic acid ester is not critical and can be varied widely. Where substantial excess of carbamic acid ester is utilized the amount of catalyst, based on the diol is typically 0.01 to 10 mole % and preferably about 2 to 5 mole %.

Preferably the carbamate is heated mildly to maintain it molten, from 40° C. to 150° C. being preferred. The catalyst is dissolved in the molten carbamate, and the diol is then slowly added. When the reaction is complete the mixture is treated to remove or neutralize the catalyst. Unreacted carbamate ester is then separated by distillation in partial vacuum or by drowning in water and filtration to separate insoluble urethane products from water-soluble carbamate ester.

Tertiary aralkyl urethane esters form the corresponding isocyanate by thermal cracking while splitting off the alkanol. In many cases the alcohol can usefully be recycled by reaction with urea or isocyanic acid (HNCO) to form the starting carbamate ester.

In cracking the urethane esters to form the corresponding isocyanates the catalyst must be removed or neutralized for example, with calcium oxide, sodium carbonate, sodium hydroxide and the like, which is followed by cracking of the urethane ester either neat or in high boiling solvents, such as hexadecane, diphenyl ether, diisopropyl naphthalene and the like. Cracking takes place at temperatures on the order of 150° to 350° C. splitting off the alkanol to yield the corresponding isocyanate.

This invention has particular application in the production of tertiary aralkyl polyisocyanates from tertiary polyols and carbamic acid esters by addition of the reactants to form the corresponding polyurethane esters followed by thermal cracking of the polyurethane esters to the corresponding polyisocyanates. The preparation of m- and p-tetramethyl xylylene diisocyanates is outlined as follows:

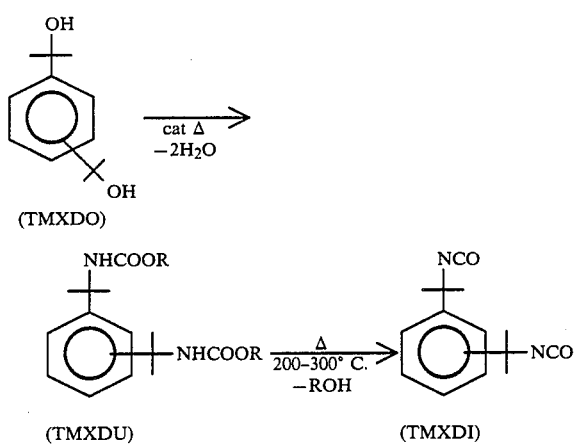

The addition reaction can also be utilized to favor the production of a monourethane, such as isopropenyl-α,α-dimethylbenzyl urethane (TMU), which can be thermally cracked to the corresponding olefinic monoisocyanate, such as isopropenyl α,α-dimethylbenzyl isocyanate (TMI). The reaction is as follows:

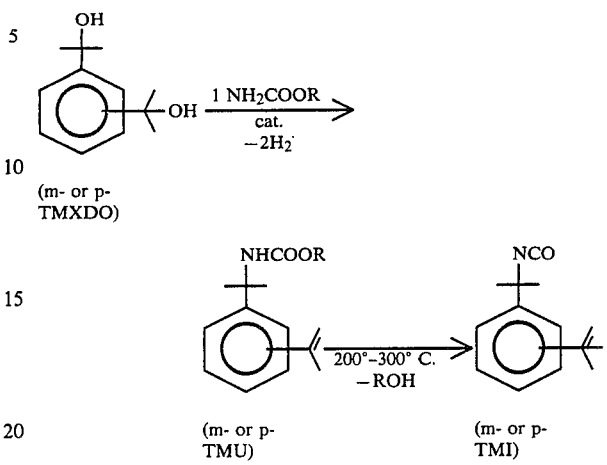

The following Examples illustrate the preparation of urethane esters in accordance with this invention and the utilization of such esters in the preparation of isocyanates useful in preparation of polyurethanes.

EXAMPLE 1

To a flask containing 58.14 g (775 mmoles) of molten methyl carbamate (85° C. oil bath) was added 0.26g (2.6 m mole) of conc. sulfuric acid. The temperature of the oil bath was then lowered to 60° C., and 18.45g (95.1 mmoles) of m-TMXDO slowly added to the reaction mixture. The reaction mixture was stirred at 65° C. for 3.5 hours., and 490 mg of anhydrous sodium carbonate added to neutralize the acid catalyst. The mixture was stirred at 65° C. for another 30 minutes and then distilled under vacuum (95° C. and 30 mm Hg) to recover unreacted methyl carbamate (41.0 g; >88% recovery). GLC analyses of the white residue showed that m-TMXDU and m-TMU were formed in 75% and 15% yield, respectively, and that 4–5% of the monohydroxy-monourethane (m-TMXUO) had been formed. The structures of the above products were verified by GC/mass spectroscopy.

EXAMPLE 2

The crude residue of Example 1 containing 75% meta-TMXDU, 15% TMU, about 4–5% hydroxy urethanes and unidentified material was readily cracked to produce the diisocyanate as follows: 10 weight percent of finely divided calcium oxide was added to a sample of the residue of Example 1 and heated to about 195° C. for one hour at ≃20 mmHg. At the end of this time pressure is reduced to 10 mmHg and the volatile diisocyanate was distilled and collected in a receiving flask. The yields of m-TMXDI and of m-tetramethyl xylylene monourethane mono isocyanate (m-TMXUI) were 30% and 17%, respectively, based on the m-TMXDU content of the residue. A yield of 12% of m-TMI, based on the m-TMU in the residue, was obtained, indicating some m-TMXUI also cracked to m-TMI.

EXAMPLE 3

Reaction of p-TMXDO and Methyl carbamate

Methyl carbamate (57.35 g, 764 m mole) were melted in a 85° C. oil bath, and to this molten methyl carbamate 19.41 g. (100 m mole) of p-TMXDO was added. The mixture turned to a clear liquid in about 15 minutes. A hot solution (85° C.) containing 0.31 g of conc. sulfuric acid and 3 g (40 m moles) of molten methyl carbamate was then added dropwise to the clear liquid. A large amount of white solid appeared in less than 10 minutes after the addition of conc. sulfuric acid was complete. At this point heating was stopped and the reaction mixture cooled to room temperature solid sodium carbonate (1.58 g) was then added. After stirring at 85° C. for 30 minutes, the reaction mixture was distilled under vacuum to recover water (>70% recovery) and methyl carbamate (80% recovery). GLC analyses of the white distillation residue indicated that p-TMU and p-TMXDU were formed in yields of 9% and 86%, respectively.

EXAMPLE 4

In another run of p-TMXDO and methyl carbamate reaction as in Example 3, instead of neutralizing the reaction mixture with solid sodium carbonate, the reaction mixture was added to 300 ml of 30% aqueous sodium carbonate solution after the reaction of carbamate and diol was complete. The resultant aqueous sodium carbonate mixture was stirred at room temperature for 30 minutes and then filtered. The solid collected was washed with water and dried. Analyses (GLC) of the solid showed that p-TMXDU and p-TMU were generated in 90% and 4% yields, respectively.

EXAMPLE 5

Cracking of Crude p-TMXDU

The distillation residue of the reaction mixture neutralized by solid sodium carbonate (Example 3) was cracked by heating the residue at 205° C. under 35 mmHg pressure in the presence of 10% by weight) calcium oxide for 50 minutes. The pressure of the system was then lowered to 5 mmHg to distill the cracking products. Based on GLC analyses the yield of p-TMXDI was 21%, TMXUI was 24%, and p-TMI was 100% (Based on p-TMXDU and p-TMU in the crude.

EXAMPLE 6

Reaction of p-TMXDO and Methyl Carbamate

The general procedure mixing the diol and carbamate reactants of Example 3 was repeated by preparing a mixture of methyl carbamate and p-TMXDO in a mole ratio of 8:1 to which 2.5 mole percent sulfuric acid was added, based on the diol. The reaction mixture was heated for 30 minutes at 85° C. and then allowed to cool to 75° C. An additional 2.5 mole percent of sulfuric acid was then added to the mixture. The reaction mixture continued to be heated for an additional three hours at 65°–75° C. The reaction mixture was then drowned in a 50% aqueous solution of KOH in an amount 10% in excess of that required to neutralize the sulfuric acid.

The reaction mixture was then heated to 180° C. under a partial vacuum of 50 mmHg to strip water and unreacted methyl carbamate. The crude product remaining contained p-TMXDU and p-TMU in a mole ratio of 6.11:1 (74.1% overall yield based on the p-TMXDO).

EXAMPLE 7

Cracking of Crude Mixture From Example 6

The crude product of Example 6 (31 grams) containing mainly p-TMXDU (81.8 mmoles, 25.2 g.) and p-TMU (13.4 mmoles, 3.12 g.) and small amounts of p-TMXDU (3.25 mmoles), p-TMI (2.8 mmoles), p-TMXDI, (0.7 mmoles) and p-TMXUI (1.3 m moles) was cracked at 203°–217° C. at 50 mmHg for 150 minutes. 10 weight percent of CaO had been added to the mixture as a cracking catalyst. Volatiles were collected as formed. GLC analysis of the distillation products indicated a yield of 29% p-TMXDI, 33% p-TMXUI, and 22% p-TMU, based on p-TMXDU in the crude mixture. Analyses further indicated a yield of p-TMI was obtained based on the p-TMU and p-TMXDU in the crude mixture.

EXAMPLE 8

Synthesis of m-TMXUO

To a flask containing 30 grams (400 mmoles) of methyl carbamate (60° C. oil bath) was added 0.13 grams (1.3 mmoles) of concentrated sulfuric acid and the mixture was stirred for 5 minutes. To the mixture was then added 9.7 grams (50 mmoles) of m-TMXDO and the temperature of the oil bath lowered to 45° C. After being stirred for 1 hour, the reaction mixture was poured into a 5% aqueous sodium carbonate solution. The solid in the aqueous solution was removed by filtration and the aqueous solution extracted several times with methylene chloride. The methylene chloride extracts were combined, dried (Na$_2$SO$_4$) and concentrated under reduced pressure. The residue of the methylene chloride extract was then purified by column chromatography (silica gel column). m-TMXUO, an oil, was isolated (1.3 grams) having the following spectroscopic properties:

| I. | IR (m$^{-1}$). | | | |
|---|---|---|---|---|
| | 3420, | O—H(s); | 3340, | N—H(s) |
| | 2970, | 2940, | C—H(s); | 1710; C=O(s) |
| | 1540, | N—H(b); | 1350, | O—H(b) |
| II. | NRM (delta ppm, CDCl$_3$) | | | |
| | 1.5 (4 CH$_3$); | 3.5 (1 OCH$_3$); | 5.2 (1NH) | |
| | 5.8 (1 OH); | 7.0–7.5 (4 aromatic H) | | |

(s): Stretching Vibration
(b): Bending Vibration

We claim:

1. A process for production of urethanes of the general formulae:

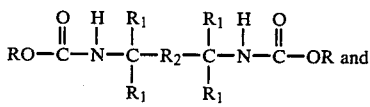

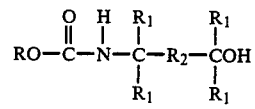

where
R is an alkyl radical derived from a lower alkanol;
R$_1$ is an alkyl radical having from 1 to 3 carbon atoms; and
R$_2$ represents an aromatic hydrocarbon moiety selected from phenyl, biphenyl and naphthalyl groups and such groups having halo, methyl and methoxy substituents and substituents of the formula:

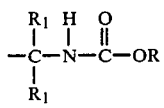

wherein R and R₁ have the same significance, which comprises admixing a diol of the formula:

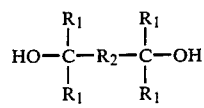

and a carbamic acid ester of a lower alkanol in the presence of an acid catalyst at a temperature between 40° and 150° C. to form said urethane in the resultant admixture.

2. The improvement according to claim 1 in which said diol is a tetramethyl xylylene diol and the carbamic acid ester is methyl carbamate.

3. The improvement according to claim 1 in which said admixture is neutralized after formation of said urethane.

4. The improvement according to claim 1 in which said carbamic acid ester is in excess of the amount of diol required to form said urethane, in which said admixture is neutralized after formation of said urethane, and in which excess, unreacted carbamic acid ester is removed after neutralization.

5. A compound of the formula:

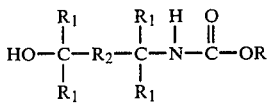

wherein
R is an alkyl radical derived from a lower alkanol;
R₁ is an alkyl radical having from 1 to 3 carbon atoms; and
R₂ represents an aromatic hydrocarbon moiety selected from phenyl, biphenyl and naphthalyl groups and such groups having halo, methyl and methoxy substituents and substituents of the formula;

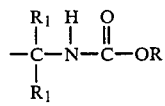

wherein R and R₁ have the same significance.

6. The improvement according to claim 1 in which said diol is di-(1-hydroxyl-1-methyl ethyl)naphthalene.

7. A process for producing tertiary aralkyl urethanes comprising reacting a tertiary aralkyl diol with a carbamic acid ester of an alkyl alcohol.

8. The process according to claim 7 wherein said reaction is carried out in the presence of an acid catalyst.

9. A process according to claim 8 wherein said acid catalyst is selected from the group consisting of sulfuric acid, toluence sulfonic, dodecylbenzene sulfonic acid, hydrocarbon slufate esters, hydrogen chloride, and boron trifluoride.

10. A process according to claim 8 wherein said acid catalyst is a Lewis or Bronstead acid.

11. A process according to claim 7 wherein said reaction is carried out in the presence of a solvent selected from group consisting of toluence, xylene, chlorobenzene and methylene dichloride.

12. A process according to claim 7 wherein said reaction is carried out at a temperature of from about ambient to about 150° C.

13. A process for production urethanes of the general formulae:

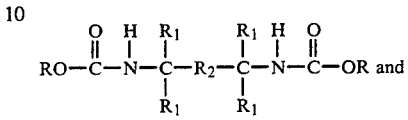

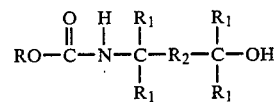

where
R is C₁–C₁₈ alkyl radical;
R₁ is an alkyl radical having from 1 to 3 carbon atoms; and
R₂ represents an aromatic hydrocarbon moiety selected from phenyl, biphenyl and naphthalyl groups and such groups having halo, methyl and methoxy substituents and substituents of the formula:

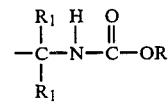

wherein R and R₁ have the same significance, which comprises admixing a diol of the formula:

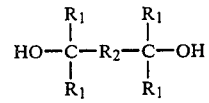

and a carbamic acid ester of a C₁–C₁₈ alkanol in the presence of an acid catalyst at a tempeature between 40° and 150° C. to form said urethane in the resultant admixture.

14. A compound of the formula:

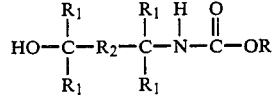

wherein
R is C₁–C₁₈ alkyl radical;
R₁ is an alkyl radical having from to 1 to 3 carbon atoms; and
R₂ represents an aromatic hydrocarbon moiety selected from phyenyl, biphenyl and naphthalyl groups and such groups having halo, methyl substituents and substituents of the formula:

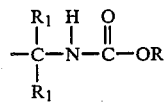

wherein R and R₁ have the same significance.

* * * * *